United States Patent [19]

Angevine et al.

[11] Patent Number: 5,395,940
[45] Date of Patent: Mar. 7, 1995

[54] SYNTHESIS OF PYRIDINE AND 3-ALKYLPYRIDINE

[75] Inventors: Philip J. Angevine, Woodbury; Cynthia T-W. Chu, Moorestown; Thomas C. Potter, Mantua, all of N.J.

[73] Assignee: Mobil Oil Corp., Fairfax, Va.

[21] Appl. No.: 73,213

[22] Filed: Jun. 7, 1993

[51] Int. Cl.$^6$ .......................................... C07D 213/09
[52] U.S. Cl. .................................... 546/250; 546/251; 502/102
[58] Field of Search ................. 546/250, 251; 502/102

[56] References Cited

U.S. PATENT DOCUMENTS

| | | | |
|---|---|---|---|
| 2,807,618 | 9/1957 | Cislak et al. | 260/290 |
| 3,946,020 | 3/1976 | Minato et al. | 260/290 P |
| 4,220,783 | 9/1980 | Chang et al. | 546/251 |
| 4,675,410 | 6/1987 | Feitler et al. | 546/251 |
| 4,866,179 | 9/1989 | Cheng et al. | 546/250 |
| 4,876,408 | 10/1989 | Ratcliffe et al. | 585/467 |
| 4,954,325 | 9/1990 | Rubin et al. | 425/328 |
| 4,992,606 | 2/1991 | Kushnerick et al. | 585/467 |
| 5,013,843 | 5/1991 | Feitler et al. | 546/251 |

OTHER PUBLICATIONS

Weisz, P. B. et al., (ed.), Advances In Catalysts, 18, 344 (1968).

Primary Examiner—Johann Richter
Assistant Examiner—Michael B. Heydorn
Attorney, Agent, or Firm—Alexander J. McKillop; Malcolm D. Keen; Dennis P. Santini

[57] ABSTRACT

An improved process is provided for selectively synthesizing pyridine and 3-alkylpyridine in high yield by reacting ammonia and a carbonyl reactant selected from the group consisting of formaldehyde, an aldehyde containing from 2 to 4 carbon atoms, a ketone containing from 3 to 5 carbon atoms, and mixtures thereof under effective conditions in the presence of a catalyst comprising an active form of a synthetic porous crystalline MCM-49 or synthetic porous crystalline material characterized by an X-ray diffraction pattern including interplanar d-spacings at $12.36\pm0.4$, $11.03\pm0.2$, $8.83\pm0.14$, $6.18\pm0.12$, $6.00\pm0.10$, $4.06\pm0.07$, $3.91\pm0.07$, and $3.42\pm0.06$ Angstroms, e.g., MCM-22, and recovering from the resulting reaction mixture a product enriched in pyridine and 3-alkylpyridine.

27 Claims, No Drawings

SYNTHESIS OF PYRIDINE AND 3-ALKYLPYRIDINE

BACKGROUND OF THE INVENTION

Field of the Invention

This invention relates to an improved method for selectively synthesizing pyridine and 3-alkylpyridine, e.g., 3-picoline, by reaction of ammonia and a carbonyl compound selected from the group consisting of formaldehyde, aldehydes containing from 2 to 4 carbon atoms, and ketones containing from 3 to 5 carbon atoms in the presence of catalyst comprising a synthetic porous crystalline material. The improvement of the present invention involves increased yield and pyridine and 3-alkylpyridine, e.g., 3-picoline, product, and is realized by the required use as catalyst of a composition comprising a specific synthetic porous crystalline material, such as, for example, MCM-49, or one characterized by an X-ray diffraction pattern including interplanar d-spacings at 12.36±0.4, 11.03±0.2, 8.83±0.14, 6.18±0.12, 6.00±0.10, 4.06±0.07, 3.91±0.07, and 3.42±0.06 Angstroms, e.g., MCM-22.

Another aspect of this invention involves manufacture of 3-pyridinecarboxylic acid, i.e., nicotinic acid, by reaction of 3-picoline recovered from the product of the above reaction with an oxidative reagent, such as, for example, $KMnO_4$.

Description of Prior Art

Reaction of acetaldehyde or certain other low molecular weight aldehydes and ammonia either in the absence or presence of methanol and/or formaldehyde to yield pyridine and alkyl derivatives thereof has been carried out in the presence of amorphous silica-alumina composites containing various promoters. See, for example, U.S. Pat. Nos. 2,807,618 and 3,946,020. The yields of desired products using the latter catalysts have been poor. Alkylpyridines have also been synthesized, as reported in *Advances in Catalysis*, 18, 344 (1968), by passing gaseous acetaldehyde and ammonia over the crystalline aluminosilicates NaX and H-mordenite. While initial conversion utilizing these materials as catalysts was high, catalyst deactivation by coking was rapid, providing a commercially unattractive system, characterized by poor catalytic stability.

The next step in the progression of pyridine and alkylpyridine synthesis was the discovery that the synthetic crystalline zeolites having an intermediate pore size as measured by the Constraint Index of the zeolite being between 1 and 12, e.g., ZSM-5, provided commercially useful yields and product selectivities. U.S. Pat. No. 4,220,783 was pioneer in this discovery, teaching synthesis of pyridine and alkylpyridines by reacting ammonia and a carbonyl reactant which is an aldehyde containing 2 to 4 carbon atoms, a ketone containing 3 to 5 carbon atoms or mixtures of said aldehydes and/or ketones under effective conditions in the presence of a catalyst comprising a crystalline aluminosilicate zeolite having been ion exchanged with cadmium and having a silica to alumina ratio of at least about 12 and a Constraint Index within the approximate range of 1 to 12.

Use of the same crystalline material catalyst component as in U.S. Pat. No. 4,220,783, i.e., having a Constraint Index of from 1 to 12, e.g., ZSM-5, in a fluidized or otherwise movable bed reactor is taught in U.S. Pat. No. 4,675,410. U.S. Pat. No. 4,866,179 teaches synthesis of pyridine by reaction of ammonia and a carbonyl compound, preferably with added hydrogen, over catalyst comprising a crystalline aluminosilicate zeolite which has been ion exchanged with a Group VIII metal of the Periodic Table. The crystalline aluminosilicate zeolite has a silica to alumina mole rate of at least 15, preferably 30 to 200, a Constraint Index of from 4 to 12, e.g., ZSM-5, and the process provides a high and selective yield of pyridine.

U.S. Pat. No. 5,013,843 teaches addition of a third aldehyde or ketone to a binary mixture of aldehydes and/or ketones used in preparing mixtures of pyridine and alkyl-substituted pyridines in large scale continuous processes. In a preferred system, propionaldehyde is added to a binary mixture of acetaldehyde and formaldehyde to produce beta-pyridine and pyridine. The catalyst for this process is a crystalline aluminosilicate zeolite in the acidic form having a Constraint Index of from 1 to 12, e.g., ZSM-5.

Applicants know of no prior art teaching the present improvement in selective synthesis of pyridine and 3-alkylpyridine, especially 3-picoline, over catalyst comprising crystals of the presently required zeolite.

SUMMARY OF THE INVENTION

In accordance with the present invention, there is provided an improved process for selectively synthesizing in high yield pyridine and 3-alkylpyridine, e.g., 3-picoline, by reacting ammonia and a carbonyl compound constituting formaldehyde, an aldehyde of 2 to 4 carbon atoms, or a ketone of 3 to 5 carbon atoms in the presence of a catalyst comprising an active form of specific synthetic porous crystalline material, such as, for example, MCM-49, or one characterized by an X-ray diffraction pattern including interplanar d-spacings at 12.36±0.4, 11.03±0.2, 8.83±0.14, 6.18±0.12, 6.00±0.10, 4.06±0.07, 3.91±0.07, and 3.42±0.06 Angstroms, e.g., MCM-22. This catalyst has been found to afford significant improvement in product yield, and in selectivity for the production of pyridine and 3-alkyl derivatives of pyridine over the use of the aforenoted prior art catalyst materials.

Crystalline catalyst component materials useful for the improvement of the present invention are described in U.S. Pat. No. 4,992,606, incorporated entirely herein by reference. U.S. Pat. No. 5,236,575, incorporated entirely herein by reference, describes MCM-49, another synthetic crystalline material useful as a catalyst component for the present process.

EMBODIMENTS

In its calcined form, the synthetic porous crystalline material component employed in the catalyst composition used in the process of this invention may be characterized by an X-ray diffraction pattern including the following lines:

TABLE A

| Interplanar d-Spacing(A) | Relative Intensity, $I/I_o \times 100$ |
|---|---|
| 12.36 ± 0.4 | m-vs |
| 11.03 ± 0.2 | m-s |
| 8.83 ± 0.14 | m-vs |
| 6.18 ± 0.12 | m-vs |
| 6.00 ± 0.10 | w-m |
| 4.06 ± 0.07 | w-s |
| 3.91 ± 0.07 | m-vs |
| 3.42 ± 0.06 | vs |

Alternatively, it may be characterized by an X-ray diffraction pattern in its calcined form including the following lines:

TABLE B

| Interplanar d-Spacing(A) | Relative Intensity, $I/I_o \times 100$ |
|---|---|
| 30.0 ± 2.2 | w-m |
| 22.1 ± 1.3 | w |
| 12.36 ± 0.4 | m-vs |
| 11.03 ± 0.2 | m-s |
| 8.83 ± 0.14 | m-vs |
| 6.18 ± 0.12 | m-vs |
| 6.00 ± 0.10 | w-m |
| 4.06 ± 0.07 | w-s |
| 3.91 ± 0.07 | m-vs |
| 3.42 ± 0.06 | vs |

More specifically, the calcined form may be characterized by an X-ray diffraction pattern including the following lines:

TABLE C

| Interplanar d-Spacing(A) | Relative Intensity, $I/I_o \times 100$ |
|---|---|
| 12.36 ± 0.4 | m-vs |
| 11.03 ± 0.2 | m-s |
| 8.83 ± 0.14 | m-vs |
| 6.86 ± 0.14 | w-m |
| 6.18 ± 0.12 | m-vs |
| 6.00 ± 0.10 | w-m |
| 5.54 ± 0.10 | w-m |
| 4.92 ± 0.09 | w |
| 4.64 ± 0.08 | w |
| 4.41 ± 0.08 | w-m |
| 4.25 ± 0.08 | w |
| 4.10 ± 0.07 | w-s |
| 4.06 ± 0.07 | w-s |
| 3.91 ± 0.07 | m-vs |
| 3.75 ± 0.06 | w-m |
| 3.56 ± 0.06 | w-m |
| 3.42 ± 0.06 | vs |
| 3.30 ± 0.05 | w-m |
| 3.20 ± 0.05 | w-m |
| 3.14 ± 0.05 | w-m |
| 3.07 ± 0.05 | w |
| 2.99 ± 0.05 | w |
| 2.82 ± 0.05 | w |
| 2.78 ± 0.05 | w |
| 2.68 ± 0.05 | w |
| 2.59 ± 0.05 | w |

Most specifically, it may be characterized in its calcined form by an X-ray diffraction pattern including the following lines:

TABLE D

| Interplanar d-Spacing(A) | Relative Intensity, $I/I_o \times 100$ |
|---|---|
| 30.0 ± 2.2 | w-m |
| 22.1 ± 1.3 | w |
| 12.36 ± 0.4 | m-vs |
| 11.03 ± 0.2 | m-s |
| 8.83 ± 0.14 | m-vs |
| 6.86 ± 0.14 | w-m |
| 6.18 ± 0.12 | m-vs |
| 6.00 ± 0.10 | w-m |
| 5.54 ± 0.10 | w-m |
| 4.92 ± 0.09 | w |
| 4.64 ± 0.08 | w |
| 4.41 ± 0.08 | w-m |
| 4.25 ± 0.08 | w |
| 4.10 ± 0.07 | w-s |
| 4.06 ± 0.07 | w-s |
| 3.91 ± 0.07 | m-vs |
| 3.75 ± 0.06 | w-m |
| 3.56 ± 0.06 | w-m |
| 3.42 ± 0.06 | vs |
| 3.30 ± 0.05 | w-m |
| 3.20 ± 0.05 | w-m |
| 3.14 ± 0.05 | w-m |

TABLE D-continued

| Interplanar d-Spacing(A) | Relative Intensity, $I/I_o \times 100$ |
|---|---|
| 3.07 ± 0.05 | w |
| 2.99 ± 0.05 | w |
| 2.82 ± 0.05 | w |
| 2.78 ± 0.05 | w |
| 2.68 ± 0.05 | w |
| 2.59 ± 0.05 | w |

Examples of such porous crystalline materials include the PSH-3 composition of U.S. Pat. No. 4,439,409, incorporated herein by reference, and MCM-22 of U.S. Pat. No. 4,954,325, incorporated herein by reference.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component, e.g., hexamethyleneimine. The Na and R components are associated with the zeolite as a result of their presence during crystallization, and are easily removed by post-crystallization methods hereinafter more particularly described.

Zeolite MCM-22 is thermally stable and exhibits a high surface area greater than about 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include hydrogen ions and hydrogen precursor, e.g., ammonium, ions. In its calcined form, zeolite MCM-22 appears to be made up of a single crystal phase with little or no detectable impurity crystal phases and has an X-ray diffraction pattern including the lines listed in above Tables A-D.

The crystalline material MCM-49 for use as catalyst component in this invention is described in U.S. patent application Ser. No. 5,236,575, entirely incorporated herein by reference, and has a composition involving the molar relationship:

$$X_2O_3:(n)YO_2,$$

wherein X is a trivalent element, such as aluminum, boron, iron and/or gallium, preferably aluminum; Y is a tetravalent element such as silicon, titanium, and/or germanium, preferably silicon; and n is less than about 35, e.g., from 2 to less than about 35, usually from about 10 to less than about 35, more usually from about 15 to about 31. In the as-synthesized form, the material has a formula, on an anhydrous basis and in terms of moles of oxides per n moles of $YO_2$, as follows:

(0.1–0.6)$M_2O$:(1–4)$R$:$X_2O_3$:$nYO_2$ wherein M is an alkali or alkaline earth metal, and R is an organic moiety. The M and R components are associated with the material as a result of their presence during crystallization, and are easily removed by post-crystallization methods hereinafter more particularly described.

The MCM-49 for use in the invention is thermally stable and in the calcined form exhibits high surface area (greater than 400 m²/gm) and unusually large sorption capacity when compared to previously described materials such as calcined PSH-3 (U.S. Pat. No. 4,439,409) and SSZ-25 (U.S. Pat. No. 4,826,667) having similar X-ray diffraction patterns. To the extent desired, the original sodium cations of the as-synthesized MCM-49 material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

In the as-synthesized form, the crystalline MCM-49 material for use in the invention appears to be a single crystalline phase. It can be prepared in essentially pure form with little or no detectable impurity crystal phases and has an X-ray diffraction pattern which is distinguished from the patterns of other known as-synthesized or thermally treated crystalline materials by the lines listed in Table E below:

TABLE E

| Interplanar d-Spacing(A) | Relative Intensity, $I/I_o \times 100$ |
|---|---|
| 13.15 ± 0.26 | w-s* |
| 12.49 ± 0.24 | vs |
| 11.19 ± 0.22 | m-s |
| 6.43 ± 0.12 | w |
| 4.98 ± 0.10 | w |
| 4.69 ± 0.09 | w |
| 3.44 ± 0.07 | vs |
| 3.24 ± 0.06 | w |

*shoulder

The X-ray diffraction peak at 13.15±0.26 Angstrom Units (A) is usually not fully resolved for MCM-49 from the intense peak at 12.49±0.24, and is observed as a shoulder of this intense peak. For this reason, the precise intensity and position of the 13.15±0.26 Angstroms peak are difficult to determine within the stated range.

In its calcined form, the crystalline MCM-49 material for use in the invention is a single crystal phase with little or no detectable impurity crystal phases having an X-ray diffraction pattern which is not easily distinguished from that of MCM-22, but is readily distinguishable from the patterns of other known crystalline materials. The X-ray diffraction pattern of the calcined form of MCM-49 includes the lines listed in Table F below:

TABLE F

| Interplanar d-Spacing(A) | Relative Intensity, $I/I_o \times 100$ |
|---|---|
| 12.41 ± 0.24 | vs |
| 11.10 ± 0.22 | s |
| 8.89 ± 0.17 | m-s |
| 6.89 ± 0.13 | w |
| 6.19 ± 0.12 | m |
| 6.01 ± 0.12 | w |
| 5.56 ± 0.11 | w |
| 4.96 ± 0.10 | w |
| 4.67 ± 0.09 | w |
| 4.59 ± 0.09 | w |
| 4.39 ± 0.09 | w |
| 4.12 ± 0.08 | w |
| 4.07 ± 0.08 | w-m |
| 3.92 ± 0.08 | w-m |
| 3.75 ± 0.07 | w-m |
| 3.57 ± 0.07 | w |
| 3.43 ± 0.07 | s-vs |
| 3.31 ± 0.06 | w |
| 3.21 ± 0.06 | w |
| 3.12 ± 0.06 | w |
| 3.07 ± 0.06 | w |
| 2.83 ± 0.05 | w |
| 2.78 ± 0.05 | w |
| 2.69 ± 0.05 | w |
| 2.47 ± 0.05 | w |
| 2.42 ± 0.05 | w |
| 2.38 ± 0.05 | w |

The above X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (60–100), s=strong (40–60), m=medium (20–40) and w=weak (0–20). It should be understood that diffraction data listed as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-49 with similar materials, e.g., MCM-22 and PSH-3.

The significance of differences in the X-ray diffraction patterns of these materials can be explained from a knowledge of the structures of the materials. MCM-22 and PSH-3 are members of an unusual family of materials because, upon calcination, there are changes in the X-ray diffraction pattern that can be explained by a significant change in one axial dimension. This is indicative of a profound change in the bonding within the materials and not a simple loss of the organic material. The precursor members of this family can be clearly distinguished by X-ray diffraction from the calcined members. An examination of the X-ray diffraction patterns of both precursor and calcined forms shows a number of reflections with very similar position and intensity, while other peaks are different. Some of these differences are directly related to the changes in the axial dimension and bonding.

The as-synthesized MCM-49 has an axial dimension similar to those of the calcined members of the family and, hence, there are similarities in their X-ray diffraction patterns. Nevertheless, the MCM-49 axial dimension is different from that observed in the calcined materials. For example, the changes in axial dimensions in MCM-22 can be determined from the positions of peaks particularly sensitive to these changes. Two such peaks occur at ~13.5 Angstroms and ~6.75 Angstroms in precursor MCM-22, at ~12.8 Angstroms and ~6.4 Angstroms in as-synthesized MCM-49, and at ~12.6 Angstroms and ~6.30 Angstroms in the calcined MCM-22. Unfortunately, the ~12.8 Angstroms peak in MCM-49 is very close to the intense ~12.4 Angstroms peak observed for all three materials, and is frequently not fully separated from it. Likewise, the ~12.6 Angstroms peak of the calcined MCM-22 material is usually only visible as a shoulder on the intense ~12.4 Angstroms peak. FIG. 1 shows the same segment of the diffraction patterns of precursor MCM-22, calcined MCM-22, and MCM-49; the position of the ~6.6–6.3 Angstroms peak is indicated in each segment by an asterisk. Because the ~6.4 Angstroms peak is unobscured in MCM-49, it was chosen as a better means of distinguishing MCM-49 from the calcined forms of MCM-22 and PSH-3 rather than the much stronger ~12.8 Angstroms peak. Table E lists all diffraction peaks characteristic of MCM-49.

MCM-49 can be prepared from a reaction mixture containing sources of alkali or alkaline earth metal (M), e.g. sodium or potassium, cation, an oxide of trivalent element X, e.g. aluminum, an oxide of tetravalent element Y, e.g. silicon, directing agent (R), and water, said reaction mixture having a composition, in terms of mole ratios of oxides, within the following ranges:

| Reactants | Useful | Preferred |
|---|---|---|
| $YO_2/X_2O_3$ | 12 to <35 | 18 to 31 |
| $H_2O/YO_2$ | 10 to 70 | 15 to 40 |
| $OH^-/YO_2$ | 0.05 to 0.50 | 0.05 to 0.30 |
| $M/YO_2$ | 0.05 to 3.0 | 0.05 to 1.0 |
| $R/YO_2$ | 0.2 to 1.0 | 0.3 to 0.5 |

In this synthesis method, if more than one X component is present, at least one must be present such that the $YO_2/X_2O_3$ molar ratio thereof is less than about 35. For example, if aluminum oxide and gallium oxide components are used in the reaction mixture, at least one of the $YO_2/Al_2O_3$ and $YO_2/Ga_2O_3$ molar ratios must be less than about 35. If only aluminum oxide has been added to the reaction mixture as a source of X, the $YO_2/Al_2O_3$ ratio must be less than about 35.

In the above synthesis method, the source of $YO_2$ must be comprised predominately of solid $YO_2$, for example at least about 30 wt. % solid $YO_2$ in order to obtain the crystal product of the invention. Where $YO_2$ is silica, the use of a silica source containing at least about 30 wt. % solid silica, e.g. Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystalline MCM-49 formation from the above mixture. Preferably, therefore, the $YO_2$, e.g. silica, source contains at least about 30 wt. % solid $YO_2$, e.g. silica, and more preferably at least about 40 wt. % solid $YO_2$, e.g. silica.

Directing agent R is selected from the group consisting of cycloalkylamine, azacycloalkane, diazacycloalkane, and mixtures thereof, alkyl comprising from 5 to 8 carbon atoms. Non-limiting examples of R include cyclopentylamine, cyclohexylamine, cycloheptylamine, hexamethyleneimine, heptamethyleneimine, homopiperazine, and combinations thereof.

Crystallization of MCM-49 crystalline material can be carried out at either static or stirred conditions in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g. from about 24 hours to about 60 days. Thereafter, the crystals are separated from the liquid and recovered.

It should be realized that the reaction mixture components can be supplied by more than one source. The reaction mixture can be prepared either batchwise or continuously. Crystal size and crystallization time of MCM-49 crystalline material will vary with the nature of the reaction mixture employed and the crystallization conditions.

Synthesis of MCM-49 may be facilitated by the presence of at least 0.01 percent, preferably 0.10 percent and still more preferably 1 percent, seed crystals (based on total weight) of crystalline product. Useful seed crystals include those having the structure of MCM-49.

Prior to its use as catalyst, the zeolite crystals should be subjected to thermal treatment to remove part or all of any organic constituent present therein. This thermal treatment is generally performed by heating at a temperature of at least about 370° C. for at least 1 minute and generally not longer than 20 hours. While subatmospheric pressure can be employed for the thermal treatment, atmospheric pressure is preferred simply for reasons of convenience.

The zeolite crystals for use herein can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the crystalline material with another material which is resistant to the temperatures and other conditions employed in the condensation process of this invention. Such materials include active and inactive materials and synthetic or naturally occurring zeolites as well as inorganic materials such as clays, silica and/or metal oxides such as alumina, magnesia, zirconia, thoria, beryllia, and/or titania. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that the products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with zeolite crystals include the montmorillonite and kaolin families which include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. It may also be advantageous to provide at least a part of the foregoing matrix materials in colloidal form so as to facilitate extrusion of the bound catalyst components.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The carbonyl reactant taking part in the catalytic reaction described herein may be formaldehyde, an aldehyde containing 2 to 4 carbon atoms, a ketone containing 3 to 5 carbon atoms, or mixtures thereof. Representative reactant aldehydes include acetaldehyde, propionaldehyde, acrolein, butyraldehyde, and crotonaldehyde. Representative reactant ketones include acetone, methyl ethyl ketone, diethyl ketone, and methyl propyl ketone. Mixtures, of course, may be used as reactants in the process of this invention.

The present improved process involving reaction between carbonyl compound and ammonia is effectively carried out at a temperature from about 285° C. to about 600° C., preferably from about 340° C. to about 550° C., at a pressure from about 0.2 atmosphere to about 20 atmospheres, preferably from about 0.8 atmosphere to about 10 atmospheres, utilizing a gas hourly space velocity of from about 200 to about 20,000 $hr^{-1}$, and preferably from about 300 to about 5,000 $hr^{-1}$.

The mole ratio of ammonia to carbonyl reactant in the reaction mixture employed will generally be between about 0.5 and about 10 and more usually between about 1 and about 5. Hydrogen may, if desired, be added to the reaction at the rate of from 0 (no added hydrogen) to about 5,000 cc/hour, preferably from 0 to about 1,000 cc/hour.

At the completion of the reaction, the product may be separated into its desired components by any feasible means, e.g., by fractionation, to recover a product containing the pyridine or the 3-alkylpyridine compound.

Of the 3-alkylpyridine compounds selectively produced by way of the present invention, 3-picoline is an important intermediate in the manufacture of 3-pyridinecarboxylic acid, i.e., nicotinic acid, and other medicinal, agricultural, and chemical products. These products have important pharmaceutical significance as well as being used as additives in food and feeds. Another of the compounds selectively produced by way of the present invention is pyridine. This latter compound is an important chemical used in the manufacture of herbicides and pesticides. It is also used as a solvent in the textile industry.

An important aspect of the present invention involves synthesis of 3-pyridinecarboxylic acid by the integrated process comprising (1) synthesis of 3-picoline by reacting ammonia, acetaldehyde and formaldehyde in the presence of catalyst comprising synthetic porous crystalline material MCM-49 and/or one characterized by an X-ray diffraction pattern including interplanar d-spacings at 12.36±0.4, 11.03±0.2, 8.83±0.14, 6.18±0.12, 6.00±0.10, 4.06±0.07, 3.91±0.07, and 3.42±0.06 Angstroms at reaction conditions including a temperature of from about 285° C. to about 600° C., a pressure of from about 0.2 atmospheres to about 20 atmospheres and a gas hourly space velocity of from about 200 $hr^{-1}$ to about 20,000 $hr^{-1}$, (2) recovering the 3-picoline product of the synthesis step (1), and oxidizing the 3-picoline of step (2) by, for example, contacting same with an oxidative reagent, such as $KMnO_4$ or the like.

The following examples will serve to illustrate the present invention without limiting same.

EXAMPLE 1

Zeolite MCM-22 was prepared as in U.S. Pat. No. 4,954,325, incorporated herein by reference, combined with alumina binder and extruded to form 65 wt. % MCM-22/35 wt. % alumina extrudate catalyst. The hydrogen form of this material was prepared by ammonium exchange (i.e., with 1N $NH_4NO_3$ at room temperature) followed by calcination at 538° C. in air.

A sample of the MCM-22 catalyst was loaded into a micro-reactor and heated to 427° C. under a nitrogen atmosphere. The reaction was run at 427° C. with ammonia flow of 578 cc/hour, hydrogen flow of 253 cc/hour, and with a mixture of 1 wt. portion of acetaldehyde and 1.3 wt. portion of formaline (37 wt. % formaldehyde) at 3.2 cc/hour. The GHSV ($NH_3$) was 580 $hr^{-1}$. The reaction mixture molar ratio of acetaldehyde/formaldehyde/$NH_3$/$H_2$ was 1.4/1/3.6/1.6. After an hour on stream, the products were condensed and analyzed.

The pyridine and 2-, 3-, and 4-picoline yields were obtained by analyzing the liquid product on a 30 m×0.25 mm ID fused silica gas chromatographic column with a 0.25 μm thick polyethylene glycol-acid modified (DB-FFAP) phase. Gas chromatography-mass spectrometry was used to confirm the identity and homogeneity of the chromatographic peaks. The pyridine and picolines were quantified using quinoline as the internal standard. Results are summarized in Table G.

EXAMPLE 2

For comparison purposes, zeolite ZSM-5 was prepared as in European Patent No. 130,809, incorporated herein by reference, combined with alumina binder and extruded to form 65 wt. % ZSM-5/35 wt. % alumina extrudate catalyst. The hydrogen form of this material was prepared by ammonium exchange (i.e., with 1N NH4NO3 at room temperature) followed by calcination at 538° C. in air. ZSM-5 has been the preferred zeolite used commercially for pyridine synthesis.

A sample of the ZSM-5 catalyst was loaded into the micro-reactor and the reaction was run and the product analyzed under the same conditions as described in Example 1. Results are summarized in Table G.

TABLE G

| Example | 1 | 2 |
|---|---|---|
| Catalyst | MCM-22 | ZSM-5 |
| Product Selectivity, wt. % | | |
| Pyridine | 9.3 | 9.5 |
| 2-Picoline | 0.6 | 0.6 |
| 3-Picoline | 4.1 | 3.7 |
| 4-Picoline | 0.9 | 0.7 |
| Total Picolines, wt. % | 5.6 | 5.0 |
| 3-Picoline, % per charge | 4.47 | 3.58 |
| Pyridine, % per charge | 10.14 | 9.18 |

These examples confirm the improvement of the present invention. Catalysts comprising the presently required zeolite are significantly more active and more selective than catalyst comprising ZSM-5 for the process of this invention.

EXAMPLE 3

A sample of recovered 3-picoline from Example 1 is contacted with the oxidative reagent KMnO4 in an organic solvent at refluxing temperature for 2 hours. The reaction is then treated with water and the reactants filtered. Product pyridine-3-carboxylic acid, i.e., nicotinic acid, is then extracted from the reaction mixture, e.g., with ethylacetate, and recovered.

What is claimed is:

1. In a process which comprises reacting ammonia and a carbonyl reactant selected from the group consisting of formaldehyde, aldehydes containing from 2 to 4 carbon atoms, and ketones containing from 3 to 5 carbon atoms, or mixtures thereof under suitable reaction conditions of temperature, pressure, and space velocity to produce a product comprising pyridine and 3-alkylpyridine in the presence of a catalyst comprising synthetic porous crystalline material, the improvement wherein said catalyst comprises an active form of synthetic porous crystalline MCM-49 or synthetic porous crystalline material characterized by an X-ray diffraction pattern including interplanar d-spacings at 12.36±0.4, 11.03±0.2, 8.83±0.14, 6.18±0.12, 6.00±0.10, 4.06±0.07, 3.91±0.07, and 3.42±0.06 Angstroms, said reaction conditions including a temperature of from about 285° C. to about 600° C., a pressure of from about 0.2 atmosphere to about 20 atmospheres, and a gas hourly space velocity of from about 200 hr$^{-1}$ to about 20,000 hr$^{-1}$.

2. The process of claim 1 wherein the synthetic porous crystalline material is characterized by an X-ray diffraction pattern including interplanar d-spacings at 30±2.2, 22.1±1.3, 12.36±0.4, 11.03±0.2, 8.83±0.14, 6.18±0.12, 6.00±0.10, 4.06±0.07, 3.91±0.07, and 3.42±0.06 Angstroms.

3. The process of claim 1 wherein the synthetic porous crystalline material is characterized by an X-ray diffraction pattern including interplanar d-spacings at 12.36±0.4, 11.03±0.2, 8.83±0.14, 6.86±0.14, 6.18±0.12, 6.00±0.10, 5.54±0.10, 4.92±0.09, 4.64±0.08, 4.41±0.08, 4.25±0.08, 4.10±0.07, 4.06±0.07, 3.91±0.07, 3.75±0.06, 3.56±0.06, 3.42±0.06, 3.30±0.05, 3.20±0.05, 3.14±0.05, 3.07±0.05, 2.99±0.05, 2.82±0.05, 2.78±0.05, 2.68±0.05, and 2.59±0.05 Angstroms.

4. The process of claim 1 wherein the synthetic porous crystalline material is characterized by an X-ray diffraction pattern including interplanar d-spacings at 30.0±2.2, 22.1±1.3, 12.36±0.4, 11.03±0.2, 8.83±0.14, 6.86±0.14, 6.18±0.12, 6.00±0.10, 5.54±0.10, 4.92±0.09, 4.64±0.08, 4.41±0.08, 4.25±0.08, 4.10±0.07, 4.06±0.07, 3.91±0.07, 3.75±0.06, 3.56±0.06, 3.42±0.06, 3.30±0.05, 3.20±0.05, 3.14±0.05, 3.07±0.05, 2.99±0.05, 2.82±0.05, 2.78±0.05, 2.68±0.05, and 2.59±0.05 Angstroms.

5. The process of claim 1 wherein the synthetic porous crystalline material is MCM-49 characterized by an X-ray diffraction pattern including interplanar d-spacings at 13.15±0.26, 12.49±0.24, 11.19±0.22, 6.43±0.12, 4.98±0.10, 4.69±0.09, 3.44±0.07, and 3.24±0.06 Angstroms.

6. The process of claim 1 wherein the synthetic porous crystalline material is MCM-49 characterized by an X-ray diffraction pattern including interplanar d-spacings at 12.41±0.24, 11.10±0.22, 8.89±0.17, 6.89±0.13, 6.19±0.12, 6.01±0.12, 5.56±0.11, 4.96±0.10, 4.67±0.09, 4.59±0.09, 4.39±0.09, 4.12±0.08, 4.07±0.08, 3.92±0.08, 3.75±0.07, 3.57±0.07, 3.43±0.07, 3.31±0.06, 3.21±0.06, 3.12±0.06, 3.07±0.06, 2.83±0.05, 2.78±0.05, 2.69±0.05, 2.47±0.05, 2.42±0.05, and 2.38±0.05 Angstroms.

7. The process of claim 1 wherein the synthetic porous crystalline material has a composition comprising the molar relationship:

$$X_2O_3:(n)YO_2,$$

wherein n is at least 10, X is a trivalent element selected from the group consisting of aluminum, boron, iron, and gallium, or combinations thereof, and Y is a tetravalent element selected from the group consisting of silicon, and germanium, or combinations thereof.

8. The process of claim 2 wherein the synthetic porous crystalline material has a composition comprising the molar relationship:

$$X_2O_3:(n)YO_2,$$

wherein n is at least 10, X is a trivalent element selected from the group consisting of aluminum, boron, iron, and gallium, or combinations thereof, and Y is a tetravalent element selected from the group consisting of silicon, and germanium, or combinations thereof.

9. The process of claim 3 wherein the synthetic porous crystalline material has a composition comprising the molar relationship:

$$X_2O_3:(n)YO_2,$$

wherein n is at least 10, X is a trivalent element selected from the group consisting of aluminum, boron, iron, and gallium, or combinations thereof, and Y is a tetravalent element selected from the group consisting of silicon, and germanium, or combinations thereof.

10. The process of claim 4 wherein the synthetic porous crystalline material has a composition comprising the molar relationship:

$$X_2O_3:(n)YO_2,$$

wherein n is at least 10, X is a trivalent element selected from the group consisting of aluminum, boron, iron, and gallium, or combinations thereof, and Y is a tetravalent element selected from the group consisting of silicon, and germanium, or combinations thereof.

11. The process of claim 5 wherein the synthetic porous crystalline MCM-49 has a composition comprising the molar relationship:

$$X_2O_3:(n)YO_2,$$

wherein n is less than about 35, X is a trivalent element selected from the group consisting of aluminum, boron, iron, and gallium, or combinations thereof, and Y is a tetravalent element selected from the group consisting of silicon, and germanium, or combinations thereof.

12. The process of claim 6 wherein the synthetic porous crystalline MCM-49 has a composition comprising the molar relationship:

$$X_2O_3:(n)YO_2,$$

wherein n is less than about 35, X is a trivalent element selected from the group consisting of aluminum, boron, iron, and gallium, or combinations thereof, and Y is a tetravalent element selected from the group consisting of silicon, and germanium, or combinations thereof.

13. The process of claim 7 wherein X comprises aluminum and Y comprises silicon.

14. The process of claim 11 wherein X comprises aluminum and Y comprises silicon.

15. The process of claim 1 wherein said synthetic porous crystalline material has been treated to replace original cations, at least in part, with a cation or mixture of cations selected from the group consisting of hydrogen and hydrogen precursors.

16. The process of claim 1 wherein said synthetic porous crystalline material is combined with a matrix material.

17. The process of claim 16 wherein said matrix material is silica, magnesia, zirconia, thoria, beryllia, titania, or alumina-containing material.

18. The process of claim 1 wherein said reactant aldehydes are selected from the group consisting of acetaldehyde, propionaldehyde, acrolein, butyraldehyde, and crotonaldehyde, or mixtures thereof.

19. The process of claim 1 wherein said reactant ketones are selected from the group consisting of acetone, methyl ethyl ketone, and methyl propyl ketone, or mixtures thereof.

20. The process of claim 1 wherein said reaction conditions include addition of hydrogen at from 0 to about 5,000 cc/hour.

21. The process of claim 1 wherein said carbonyl reactant is selected from the group consisting of formaldehyde, and aldehydes containing from 2 to 4 carbon atoms, or mixtures thereof.

22. The process of claim 21 wherein said carbonyl reactant is selected from the group consisting of formaldehyde, and acetaldehyde, or mixture thereof.

23. The process of claim 1 where said reaction conditions include a temperature of from about 340° C. to about 550° C., a pressure of from about 0.8 atmosphere to about 10 atmospheres, and a gas hourly space velocity of from about 300 $hr^{-1}$ to about 5,000 $hr^{-1}$.

24. The process of claim 23 wherein said reaction conditions include addition of hydrogen at from about 0 to about 1,000 cc/hour.

25. A process for synthesizing 3-pyridinecarboxylic acid which comprises reacting a feedstock comprising ammonia, formaldehyde, and acetaldehyde under suitable conditions including a temperature of from about 285° C. to about 600° C., a pressure of from about 0.2 atmosphere to about 20 atmospheres, and a gas hourly space velocity of from about 200 $hr^{-1}$ to about 20,000 $hr^{-1}$ to produce product comprising 3-picoline in the presence of a catalyst comprising an active form of synthetic porous crystalline MCM-49 or synthetic porous crystalline material characterized by an X-ray diffraction pattern including interplanar d-spacings at 12.36±0.4, 11.03±0.2, 8.83±0.14, 6.18±0.12, 6.00±0.10, 4.06±0.07, 3.91±0.07, and 3.42±0.06 Angstroms, and oxidizing the 3-picoline to form product comprising 3-pyridinecarboxylic acid.

26. The process of claim 25 wherein said oxidizing step comprises contacting said 3-picoline with an oxidizing reagent at reflux.

27. The process of claim 26 wherein said reagent comprises $KMnO_4$.

* * * * *